United States Patent
Truitt (10) Patent No.: US 8,845,766 B2
(45) Date of Patent: Sep. 30, 2014

(54) CONDENSATION OF ALCOHOLS FOR BIOFUEL PRODUCTION

(75) Inventor: Matthew J. Truitt, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 95 days.

(21) Appl. No.: 13/351,717

(22) Filed: Jan. 17, 2012

(65) Prior Publication Data

US 2012/0186144 A1 Jul. 26, 2012

Related U.S. Application Data (60) Provisional application No. 61/436,097, filed on Jan. 25, 2011, provisional application No. 61/438,296, filed on Feb. 1, 2011.

(51) Int. Cl.
| | | |
|---|---|---|
| *C10L 1/185* | (2006.01) | |
| *C07C 41/09* | (2006.01) | |
| *C10L 10/12* | (2006.01) | |
| *C10L 10/02* | (2006.01) | |
| *C10L 1/182* | (2006.01) | |

(52) U.S. Cl.
CPC .................. *C07C 41/09* (2013.01); *C10L 10/12* (2013.01); *C10L 10/02* (2013.01); *C10L 1/1824* (2013.01); *C10L 1/1852* (2013.01)
USPC .................. 44/447; 44/448; 44/449

(58) Field of Classification Search
USPC .................. 44/447–449
See application file for complete search history.

(56) References Cited

U.S. PATENT DOCUMENTS

| | | | |
|---|---|---|---|
| 6,521,783 | B1* | 2/2003 | Wegman et al. .............. 560/232 |
| 7,049,476 | B1 | 5/2006 | O'Lenick, Jr. |
| 2008/0295393 | A1 | 12/2008 | Portilho et al. |
| 2008/0300435 | A1 | 12/2008 | Cortright et al. |
| 2008/0302011 | A1 | 12/2008 | Bizjak |
| 2010/0094062 | A1 | 4/2010 | Rabello et al. |
| 2010/0251609 | A1* | 10/2010 | Ozer et al. ...................... 44/448 |

FOREIGN PATENT DOCUMENTS

| | | |
|---|---|---|
| WO | 2009064828 | 5/2009 |
| WO | 2009081204 | 7/2009 |

OTHER PUBLICATIONS

Reinier J.J., Nel and Arno De Klerk, "Dehydration of C5-C12 Linear 1-Alcohols over n-Alumina to Fuel Ethers", Ind. Eng Chem. Res. 2009, 48, pp. 5230-5238, May 4, 2009 American Chemical Society.

(Continued)

*Primary Examiner* — Brian McCaig
(74) *Attorney, Agent, or Firm* — Phillips 66 Company (57) ABSTRACT

The present disclosure relates to methods for converting biomass-derived hydrocarbon streams into products suitable for use as fuel additives. These methods involve the acidic condensation of hydrocarbon monofunctional alcohols comprising five or six carbon atoms to form ether condensation products containing at least ten carbon atoms. The oxygenated condensation products can be separated from un-reacted alcohols and gasoline range hydrocarbons to provide an oxygenated fuel additive that may be mixed with a diesel or kerosene-type liquid hydrocarbon fuel to provide an improved fuel that may have an increased cetane number, decreased emissions of environmental pollutants during combustion, or both.

11 Claims, 4 Drawing Sheets

(56) References Cited

OTHER PUBLICATIONS

Eduardo Medina, Roger Bringue, Javier Tejero, Montserrat Iborra, Carles Fite, "Conversion of 1-Hexanol to di-n-Hexyl Ether on Acidic Catalysts", Applied Catalysts A: General 374, 2010, pp. 41-47.

Klepacova, K., et al., "tert-Butylation of Glycerol Catalyzed by Ion-Exchange Resins." Applied Catalysis A: General 294: 141-147 (2005).

Karinen, R. et al., "New Biocomponents from Glycerol" Applied Catalysis A: General 306: 128-133 (2006).

Frusteri, F., et al., "Catalytic Etherification of Glycerol by tert-Butyl Alcohol to Produce Oxygenated Additives for Diesel Fuel." Applied Catalysis A: General 367: 77-83 (2009).

Tijm, P. et al., "Effect of Oxygenated Cetane Improver on Diesel Engine Combustion & Emissions" http://www.energy.psu.edu/tr/cetane.html.

Murphy, M. et al., "Compendium of Experimental Cetane Number Data" NREL/SR-540-36805 (2004). http://www.nrel.gov/vehiclesandfuels/pdfs/sr368051.pdf.

* cited by examiner

CONDENSATION OF ALCOHOLS FOR BIOFUEL PRODUCTION

CROSS-REFERENCE TO RELATED APPLICATIONS

This application is a non-provisional application which claims benefit under 35 USC §119(e) to U.S. Provisional Patent Application Ser. No. 61/436,097 filed Jan. 25, 2011, U.S. Provisional Patent Application Ser. No. 61/438,296 filed Feb. 1, 2011, both entitled "CONDENSATION OF ALCOHOLS FOR BIOFUEL PRODUCTION", and both incorporated herein in their entirety.

STATEMENT REGARDING FEDERALLY SPONSORED RESEARCH OR DEVELOPMENT

None.

FIELD OF THE INVENTION

The present disclosure relates to the conversion of biomass to produce liquid hydrocarbon fuels. More specifically, the present disclosure relates to processes for converting alcohols originating from biomass into products suitable for use as fuel additives.

BACKGROUND

Over the last decade, there has been an increasing interest in discovering alternative sources of fuels and chemicals from resources other than petroleum. Development of non-petroleum-based fuels may provide economic and environmental benefits, while also increasing national security by decreasing reliance on non-domestic energy sources. Biomass, such as plants and animal fats, represent a major alternative source of feedstocks that can be converted into fuels. Liquid fuels derived from biomass are rapidly entering the market, driven by both need for increased national energy independence and rapid fluctuations in the cost of petroleum products. In 2007, the Energy Independence and Security Act was passed in the United States, which requires increasing quantities of bio-derived fuels to be produced over time. Similarly, the European Union directive 2003/30/EC promotes the use of biofuels or other renewable fuels. The directive has set a minimum percentage of biofuels to replace diesel or gasoline for transport purposes, such that by 2011 a 5.75% minimum proportion of Biofuels will be required in all gasoline and diesel fuels sold. Thus, it is essential to develop more efficient processes to convert bio-derived compounds into fuels that can fulfill these government mandates, as well as future global energy needs.

The carbohydrates found in plants and animals can be used to produce fuel range hydrocarbons. However, many carbohydrates (e.g., starch) are undesirable as feed stocks for creating biomass-derived fuels due to the costs associated with converting them to a usable form. The chemical structure of some carbohydrates makes them difficult to convert, and conversion processes may produce low yields of desirable products. Carbohydrates that are difficult to convert include compounds with low effective hydrogen to carbon ratios, including carbohydrates such as starches and sugars, as well as other oxygenates with low effective hydrogen ratios such as carboxylic acids and anhydrides, light glycols, glycerin and other polyols and short chain aldehydes. Therefore, development of an efficient and inexpensive process for converting one or more of these difficult-to-convert biomass feedstocks into a form suitable for use as an oxygenated fuel additive could be a significant contribution to the art and to the economy.

The first step in processing biomass is to cleave larger structures down to their component subunits. Some processes, such as acid hydrolysis, can release the smaller pentose and hexose subunits from larger structures such as cellulose and starch. Because these sugars are inherently five to six carbons in length, a complete deoxygenation process yields saturated hydrocarbons having boiling points in the gasoline "boiling-range" (i.e., about 27° C. to 190° C.). Unfortunately, limited options are available for the upgrading/conversion of saturated five and six carbon hydrocarbons, and no options currently exist for converting these materials into liquid hydrocarbon fuels that boils in the diesel-range in conventional refining units. However, partial deoxygenation of these sugars leaves some oxygen in the material, providing a variety of opportunities for upgrading due to the numerous chemical reactions that oxygenates may undergo.

Several partially-deoxygenated intermediates are available in these biomass feeds that may be converted to products useful as fuel additives. One class of intermediates includes primary alcohols derived from pentose and hexose sugars. These alcohols are not suitable for use as additives to diesel or jet fuel due to their relatively small size and low cetane number, as well as low flash points.

Condensation reactions are one way to assemble into larger compounds, which allows the conversion of small bio-derived feedstocks into larger sizes that are better-suited for use as a diesel fuel additive. Several groups have reported the conversion of certain biomass-derived feedstocks via condensation and etherification reactions. A paper by Karinen, et. al. pertains to the etherification of glycerol and isobutene, while papers by Frustieri, et. al. and Keplacova, et. al, both report methods for catalytic etherification of glycerol and tert-butyl alcohol. US2010/0094062 describes a process for the etherification of glycerol with an alkene or alkyne, followed by nitration of a remaining hydroxyl group. A portion of the process claimed in US2008/0300435 pertains to the dimerization/condensation of alcohols, but does not disclose or claim condensation to form ether products for use as oxygenated fuel additives. Finally, US2008/0302001 pertains to methods for producing biofuels that include several types of condensation reactions, including the Guerbet alcohol condensation, but not an acidic condensation of two alcohols to form an ether. To date, no methods have taught or disclosed a process for the acid condensation of a feedstock comprising alcohols containing five or six carbons to produce an ether useful as an oxygenated fuel additive.

BRIEF SUMMARY

The present disclosure provides processes through which alcohols derived from biomass containing five and six carbons can participate in condensation reactions to yield an ether product containing at least ten carbons. The mostly linear products are thus often suitable for use as oxygenated fuel additives when blended with diesel or kerosene-type fuel. Indeed, certain ethers have been shown to improve the ignition properties of transportation fuels (including increasing cetane number and reducing particulate emissions) when compared to currently-produced premium fuels. For example, a compendium by Murphy, et al. shows that a number of ethers containing eight or more carbon atoms have been calculated to have a high cetane number.

The present disclosure pertains to utilizing acid-catalyzed condensation reactions to convert biomass-derived monofunctional alcohols into ethers containing between ten and twelve carbons. The products of the process are useful as fuel additives for diesel or kerosene-type fuels without the need for any further modification. During the conventional processing of hydrocarbons to produce fuels, removing oxygen involves reacting oxygen containing compounds with hydrogen to produce water. In contrast, the chemistry behind the inventive process involves acid-catalyzed condensation reactions that do not require hydrogen for oxygen removal. Typical refining processes remove oxygen from feeds by consuming hydrogen. However, hydrogen is expensive and its production generates carbon dioxide. Thus, reducing the need for hydrogen in the process decreases operational cost associated with production of hydrogen, as well as the carbon footprint in the production of biofuels. Some oxygen from the starting material is left in the final product, resulting in the product maintaining much of its original volume. Finally, these condensation reactions may be conducted at much lower temperatures than conventional oxygen removal processes, resulting in further savings.

Certain embodiments disclosed herein provide a process for converting a biomass-derived mono-functional alcohol feedstock that comprises the steps of: (a) providing a biomass-derived feedstream comprising hydrocarbon mono-functional alcohols containing five or six carbon atoms, (b) contacting the feedstream with a catalyst in a reactor, where the contacting results in an acidic condensation reaction that converts a least a portion of the feedstream into product ether compounds that contain at least 10 carbon atoms that is suitable for use as an additive to a liquid hydrocarbon fuel.

Certain embodiments further comprise the step of combining the product ether compounds of step (b) with a liquid hydrocarbon fuel in the diesel ($C_{10}$-$C_{24}$) or kerosene-type ($C_8$-$C_{16}$) fuel boiling range to produce an improved liquid hydrocarbon fuel possessing improved combustion properties that may include increasing the cetane number of the fuel, decreasing the emission of environmental pollutants during combustion, or both.

BRIEF DESCRIPTION OF THE DRAWINGS

Advantages of the present invention will become apparent to those skilled in the art with the benefit of the following detailed description and upon reference to the accompanying drawing.

The invention is susceptible to various modifications and alternative forms, specific embodiments thereof are shown by way of example in the drawings. The drawings may not be to scale. It should be understood that the drawings and their accompanying detailed descriptions are not intended to limit the scope of the invention to the particular form disclosed, but rather, the intention is to cover all modifications, equivalents and alternatives falling within the spirit and scope of the present invention as defined by the appended claims.

DETAILED DESCRIPTION

Figure 1:
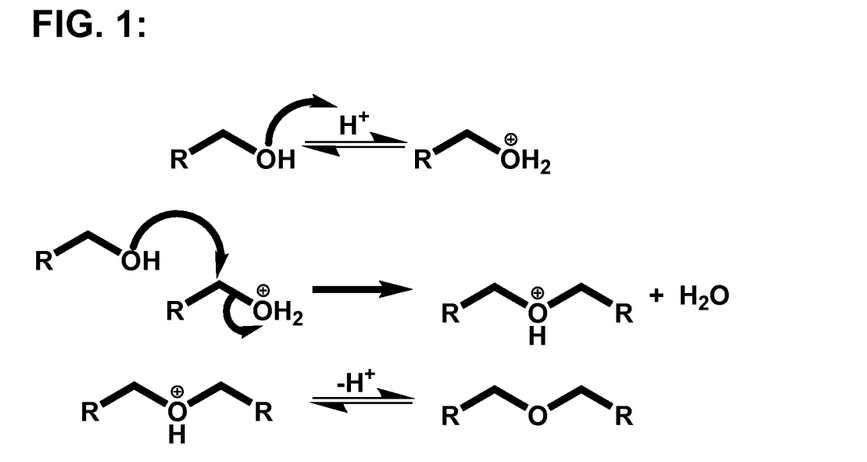
FIG. 1 is a simplified schematic depicting an acidic condensation reaction for converting two primary hydroxyl groups into an ether bond, in accordance with certain embodiments of the present disclosure.

Process conditions for conducting condensation reactions are relatively mild when compared to other industrial processes, such as conventional naphtha hydrodesulfurization, which normally requires temperatures in the range of 285° C. to 370° C. Low temperatures are advantageous to this process since at higher temperature elimination becomes a competing reaction mechanism. Elimination, like condensation, involves the removal of a small molecule from a parent, but there is no coupling associated with the reaction. Elimination results in the production of an unsaturated product (e.g., ethanol to ethylene.) While these limits exist, yields for this process are typically sufficient to operate at the commercial level for chemical production. The acidic condensation of the current disclosure could also be referred to as etherification, and is illustrated in FIG. 1. The acid catalyst donates a proton to a hydroxyl group of a first alcohol molecule, allowing a hydroxyl group from a second alcohol molecule to form an ether bond with the electrophilic carbon adjacent to the proton-accepting hydroxyl. A water molecule (and proton) are removed, and an ether bond is formed between the two alcohols. Acid-catalyzed condensation of primary alcohols in the homogeneously catalyzed case occurs via an $S_N2$ mechanism. In this type of mechanism, the transition state involves the attacking nucleophile driving off the leaving group in a concerted mechanism. This acid-catalyzed condensation reaction is distinct from the base-catalyzed condensation reaction developed by Guerbet, which instead produces branched, saturated alcohols and not ethers. Examples of the Guerbet condensation reaction being utilized to form saturated branched hydrocarbons are provided in U.S. Pat. No. 7,049,476 and US2008/0302001.

Using solid acids as catalyst, it is possible to convert monofunctional alcohols containing five or six carbons into ether products containing at least ten carbon atoms. Certain derivatives of these products fall into a category of materials termed oxygenated fuel additives. Oxygenated fuel additives are larger, predominantly linear compounds with oxygen substituted for carbon periodically along the backbone. Some have shown promise by increasing overall cetane number of the fuel, reducing particulate emissions resulting from combustion, or both. For example, a National Renewable Energy Laboratory report by Murphy, et al. shows that ethers containing at least ten carbons have been calculated to possess high cetane numbers ≥100. In addition, preliminary findings by Tijm, et al. demonstrated that several oxygen-containing polyether compounds reduced particulate emissions resulting from combustion by up to 28% when these compounds were added to premium diesel fuel at 10-11% (by weight).

The condensation reactions associated with the processes described herein are generally conducted at a temperature ranging from about 100° C. to about 300° C. Preferably, these reactions are conducted at a temperature ranging from about 120° C. to about 220° C. The condensation reactions are generally conducted at a pressure ranging from about 50 kPa to about 5000 kPa. Preferably, reactions are conducted at a pressure ranging from about 100 kPa to about 400 kPa. Additionally, condensation reactions of the present disclosure are generally conducted with a feedstream flow rate ranging from about 0.1 $h^{-1}$ weight hourly space velocity (WHSV) to about 20 $h^{-1}$ WHSV. More preferably, reactions are conducted with a feedstream flow rate ranging from about 0.5 $h^{-1}$ WHSV to about 15 $h^{-1}$ WHSV.

The strong acid digestion of biomass not only can cleave carbohydrates into smaller sugars, but also removes some of the oxygen from the product. This process leaves unsaturated, ringed products that can be hydrotreated with noble metal catalysts to produce monofunctional alcohols that may include, for example, 1-pentanol or 1-hexanol. The feedstock for the acidic condensations of the current disclosure may comprise a mixture containing one or both of these biomass-derived alcohols.

Figure 2:
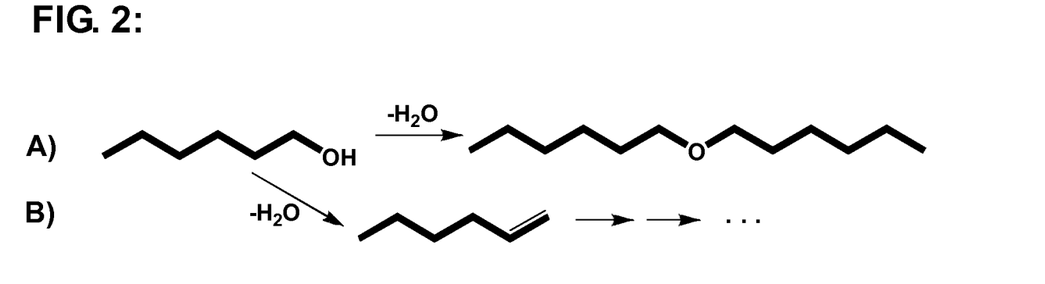
FIG. 2 is a simplified schematic depicting the acidic condensation of 1-hexanol to form dihexyl ether, in accordance with certain embodiments of the present disclosure. The dehydration of 1-hexanol to form the undesirable side-product 1-hexene is also depicted.

We utilized 1-pentanol and 1-hexanol as test compounds to demonstrate certain embodiments of the current invention, as these represent 5C-6C alcohols that can be derived from biomass in large quantities. Utilizing these mono-functional alcohols for acidic condensation to form ethers is advantageous versus using diols or polyols, as the presence of multiple hydroxyl groups makes the feedstream molecules subject to intra-molecular condensation reactions that form five-member or six-member rings (FIG. 2C). For example, with 1,5-pentanediol as feed, this cyclization produces tetrahydropyran (THP), a gasoline-range product that possesses poor fuel properties. Although 1,4-pentanediol cannot form a six-member ring such as THP, it can instead form methyltetrahydrofuran (MTHF), a five-member ring. Like THP, MTHF is a gasoline-range compound with poor fuel properties. Thus, preventing cyclization is key for the successful large-scale viability of any process that proposes to condense feeds into products useful as fuel additives.

Potential reaction pathways for a 1-hexanol feedstock in the presence of an acid catalyst are shown in FIG. 2. A condensation reaction that forms an ether product containing 12 carbon atoms is shown in FIG. 2A. A side pathway leading to the dehydration of 1-hexanol to form the olefin 1-hexene is depicted in FIG. 2B. This product may be blended into gasoline, but is not suitable for use as a fuel additive for diesel or kerosene-type fuels due to its small size.

Condensation catalysts useful with the current invention include any catalyst capable of condensing mono-functional alcohols comprising five or six carbon atoms to produce an ether containing at least 10 carbon atoms. The catalyst is an acidic catalyst capable of conducting acidic condensation reactions as depicted in FIG. 1 and FIG. 2A., and optionally, has selectivity for the formation of linear products. In certain embodiments, the catalyst is a tungstated zirconia catalyst of the formula $WO_3/ZrO_2$. Procedures for preparing such catalysts are commonly known, and may involve precipitation of $Zr(OH)_4$ followed by the loadings of tungsten oxide via incipient wetness impregnation. Alternatively, such catalysts can be obtained from commercial vendors such as, for example, Saint-Gobain NorPro (USA) or Daiichi KKK (Japan). Optionally, such catalysts can be impregnated via incipient wetness impregnation with one or more promoter metals selected from the group consisting essentially of Ru, Rh, Pd, Au, Ag, Os, Ir, Pt, Fe, Al, Cr, Ga, Co and Mg. Promoter metals are typically loaded onto the catalyst utilizing the incipient wetness impregnation technique, which is commonly known in the art. Typically, the promoter metal is loaded to between 0.1% and 1.0% by total weight of the catalyst. The catalyst is then calcined by heating to 250° C.-700° C. in excess flowing air and maintaining for a sufficient amount of time as to allow decomposition of the salt precursor. Finally, prior to use the metal loaded catalysts are reduced in excess hydrogen at moderate temperatures (200° C. to 400° C.). In instances where the catalyst is impregnated with a promoter metal, a low level of hydrogen gas (30 SCCM) is included in the reaction to ensure the promoter remains in a reduced state. Following partial catalyst deactivation (approximately 96 hrs on stream), the catalyst can be effectively reactivated by contacting with excess heated flowing air at 650° C. for 6 hrs.

In certain embodiments, the catalyst may comprise a microporous molecular sieve selected from crystalline silicoaluminophosphates and aluminosilicates (such as, for example, H-Y, H-USY, H-mordenite, or H-ZSM-5), and optionally, may be an acidic crystalline silicoaluminophosphate and aluminosilicate. Optionally, such catalysts can be impregnated via incipient wetness impregnation with one or more promoter metals selected from the group consisting essentially of Ru, Rh, Pd, Au, Ag, Os, Ir, Pt, Fe, Al, Cr, Ga, Co and Mg.

In certain embodiments, the catalyst may comprise an acidic macroreticular ion-exchange resin. Such resins are commercially available and their use is known in the art. Examples of heterogeneous acidic macroreticular ion-exchange resins include Amberlyst® resins (Dow Chemical Co., USA), Tulsion® (Thermax, Ltd., India), Nafion® (E.I. du Pont de Nemours & Co.) and equivalents. Examples of homogeneous sulfonic acid catalysts that may be used include methanesulfonic acid and para-toluenesulfonic acid.

Certain embodiments of the invention may utilize a catalyst comprising a niobium pentoxide ($Nb_2O_5$), that may be utilized alone, or in combination with one or more of the other catalysts described herein. The niobium pentoxide may be utilized unsupported or supported upon another solid. Alternatively, the niobium pentoxide may be utilized as a solid support that is impregnated with one or more of the other catalysts described herein. Techniques for preparing such catalysts comprising niobium pentoxide are known (US2008/0295393A1).

Figure 3:
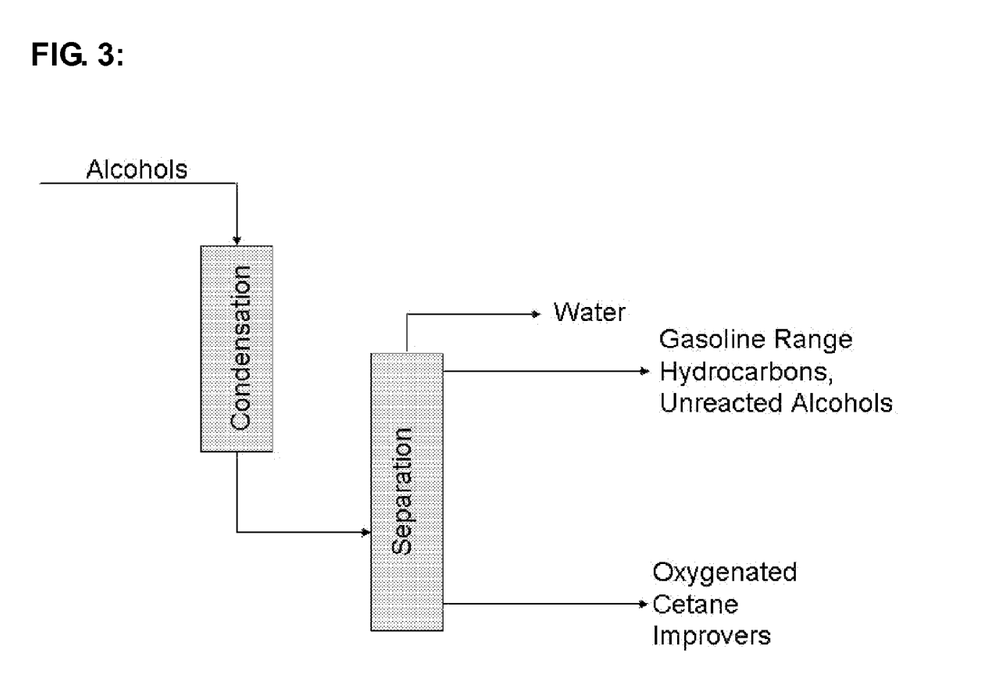
FIG. 3 is a simplified schematic depicting a process in accordance with certain embodiments of the present disclosure, comprising condensation of a mono-functional alcohol, followed by separation of the condensation products from un-reacted alcohols and gasoline boiling-range hydrocarbons. In the embodiment depicted, the alcohols and hydrocarbons are blended into gasoline products.
Figure 4:
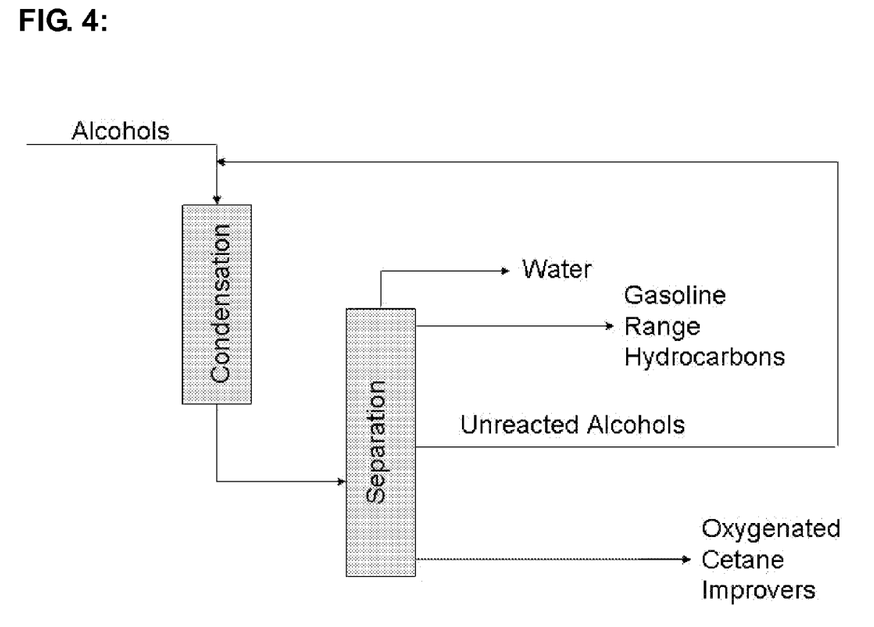
FIG. 4 is a simplified schematic in accordance with certain embodiments of the present disclosure, comprising a process for condensation of a mono-functional alcohol, followed by separation of the condensation products from un-reacted alcohols and gasoline boiling-range hydrocarbons. In the embodiment depicted, the alcohols are recycled to the condensation reaction and gasoline hydrocarbons are blended into gasoline products.

Certain embodiments provide a process by which the condensation products are separated from any un-reacted alcohols and other gasoline boiling-range hydrocarbons (FIG. 3). One option for accomplishing such separation may be to utilize a distillation apparatus. Any un-reacted alcohols or other gasoline range hydrocarbons (such as products of dehydration side-reactions to produce five or six carbon olefins) could be removed near the top of the distillation apparatus and utilized for blending into gasoline (FIG. 3), thereby preventing waste of these components. Condensation products comprising ethers containing at least ten carbon atoms would be removed near the bottom of the distillation apparatus and utilized as an oxygenated additive for blending into diesel or kerosene-type fuels (FIG. 3). Optionally, the un-reacted alcohols of the feedstream could be separately removed from the distillation apparatus at a point lower than the gasoline range side-products, allowing the un-reacted alcohols to be recycled to the condensation process (FIG. 4).

EXAMPLES

The following examples are each intended to be illustrative of a specific embodiment of the present invention in order to teach one of ordinary skill in the art how to make and use the invention. It is not intended to limit the scope of the invention in any way.

Example I

Catalytic Conversion Test Conditions: Unless otherwise noted, catalytic data were acquired using a ¾" down-flow reactor. A bed of glass beads prior to the catalyst bed preheated the feed to reaction temperature. 10 ml of catalyst were diluted in an inert material (alundum) to a constant volume of 20 mL to ensure homogeneous temperature distribution. Loaded reactors were heated using a three-zone Thermcraft furnace with independent temperature control for each zone, and temperature was set to 175° C. Liquid feed was delivered to the system by an ISCO 1000D syringe pump. The system pressure was ambient (1 atm). Gas hourly space velocity was set to 360 hr$^{-1}$. Runs were performed for 6-7 hours at a constant liquid feed rate of 10 mL/hr, using commercially obtained 1-hexanol. Liquid samples were collected at one hour intervals, and were analyzed on an Agilent 7890A gas chromatograph (GC) equipped with a HP-5 capillary column, and flame ionization detector (FID).

Example 2

Condensation of Mono-functional Alcohols to Ethers Utilizing a Tungstated-Zirconia Catalyst The conversion of a 1-hexanol feedstream into ether products suitable for use as oxygenated fuel additive was studied utilizing a commercial tungstated-zirconia catalyst obtained from Saint-Gobain NorPro (USA). The catalyst was crushed and sieved to −20/+40 mesh and diluted with alundum or alumina during each run (both of these diluents are inert at the reaction conditions utilized). 12.05 grams of catalyst were diluted in enough inert to make a 20 mL bed. 10 mL/hour of hexanol was delivered to the reactor, and 30 sccm of nitrogen gas. Conversions, yields, and selectivities were determined by averaging the values from samples taken at three different time points.

TABLE 1

Condensation of 1-hexanol Utilizing a Tungstated-Zirconia Catalyst.

| Feed Stream | | Conversion % (by wt.) | Selectivity % |
|---|---|---|---|
| 1-Pentanol | | 80% | 85% |
| 1-Hexanol | | 83% | 77% |
| 1:1 Mixture | 1-Pentanol | 78% | 86% |
| | 1-Hexanol | 85% | 72% |

DEFINITIONS

As used herein, the term "weight hourly space velocity" or "WHSV" refers to the weight hourly space velocity.

As used herein, the term "cetane" or "cetane number" refers to the cetane number of a fuel as measured by the ASTM (American Society for Testing and Materials) D613 or D6890 standard.

As used herein, the term "fuel" refers to any liquid hydrocarbon mixture used to power an engine, including gasoline, diesel and jet fuels.

As used herein, the term "environmental pollutant" may refer to any of a number of organic pollutants produced by the combustion of hydrocarbons. Predominantly, such pollutants include particulates or soot, nitrogen oxides, polycyclic aromatic hydrocarbons and carbon monoxide.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed and certain features of the invention may be utilized independently, all as would be apparent to one skilled in the art after having the benefit of this description of the invention. Changes may be made in the elements described herein without departing from the spirit and scope of the invention as described in the following claims.

REFERENCES

All of the references cited herein are expressly incorporated by reference. Incorporated references are listed again here for convenience:

1. US2010/0094062 (Rabello; Ferreiral; Menenzes); "Cetane Number Increasing Process and Additive for Diesel Fuel."
2. US2008/0300435 (Cortright; Blommel); "Synthesis of Liquid Fuels and Chemicals From Oxygenated Hydrocarbons."
3. US2008/0302001 (Koivusalmi; Piiola; Aalto) "Process for Producing Branched Hydrocarbons."
4. U.S. Pat. No. 7,049,476 (O'Lenick, Jr.) "Guerbet Polymers" (2006).
5. Klepacova, K., et al., "tert-Butylation of Glycerol Catalyzed by Ion-Exchange Resins." Applied Catalysis A: General 294: 141-147 (2005).
6. Karinen, R. et al., "New Biocomponents from Glycerol" Applied Catalysis A: General 306: 128-133 (2006).
7. Frusteri, F., et al., "Catalytic Etherification Of Glycerol By tert-Butyl Alcohol To Produce Oxygenated Additives For Diesel Fuel." Applied Catalysis A: General 367: 77-83 (2009).
8. Tijm, P. et al., "Effect of Oxygenated Cetane Improver on Diesel Engine Combustion & Emissions" http://www.energy.psu.edu/tecetane.html
9. Murphy, M. et al., "Compendium of Experimental Cetane Number Data" NREL/SR-540-36805 (2004). http://www.nrel.gov/vehiclesandfuels/pdfs/sr368051.pdf
10. US2008/0295393 (de Figueiredo Portillo, et al.) "Method for the Production of Biodiesel From Vegetable Oils and Fats, Using Heterogeneous Catalysts" (2008).

I claim:
1. A process comprising the steps of:
   (a) providing a biomass-derived feedstream comprising hydrocarbon mono-functional alcohols that contain five or six carbon atoms;
   (b) contacting the feedstream of step (a) with a catalyst in a reactor, wherein the contacting results in an acidic condensation reaction that converts a least a portion of the feedstream to condensation products, wherein said condensation products comprise at least 10 carbon atoms and at least one ether functional group, wherein the catalyst comprises a tungstated zirconia with the formula $WO_3/ZrO_2$, wherein the catalyst is impregnated with one or more promoter metals selected from the group consisting essentially of Ru, Rh, Pa, Au, Ag, Os, Ir, Pt, Fe, Al, Cr, Ga, Co and Mg.

2. The process of claim 1, wherein the contacting of step (b) is conducted at a temperature in the range of about 100° C. to about 300° C., and at a pressure in the range of about 50 kPa to about 5000 kPa.

3. The process of claim 1, wherein the contacting of step (b) is conducted at a temperature in the range of about 120° C. to about 220° C., and at a pressure in the range of about 100 kPa to about 400 kPa.

4. The process of claim 1, further comprising separating the condensation products from un-reacted alcohols and gasoline boiling-range hydrocarbons to produce a purified condensation product,
wherein the un-reacted alcohols and gasoline boiling-range hydrocarbons are mixed with gasoline, or optionally, the un-reacted alcohols are recycled to the contacting of step (b).

5. The process of claim 4, further comprising combining the purified condensation product with a diesel or kerosene-type liquid hydrocarbon fuel to produce an improved fuel,
wherein the improved fuel possesses an attribute selected from the group consisting of increased cetane number, decreased emissions of environmental pollutants during combustion and combinations thereof.

6. A process comprising the steps of:
(a) providing a biomass-derived feedstream comprising hydrocarbon mono-functional alcohols that contain five or six carbon atoms;
(b) contacting the feedstream of step (a) with a catalyst in a reactor, wherein the contacting results in an acidic condensation reaction that converts a least a portion of the feedstream to condensation products, wherein said condensation products comprise at least 10 carbon atoms and at least one ether functional group, wherein the catalyst is a microporous molecular sieve selected from the group consisting of crystalline silicoaluminophosphates and aluminosilicates, wherein the catalyst is impregnated with one or more promoter metals selected from the group consisting essentially of Ru, Rh, Pa, Au, Ag, Os, Ir, Pt, Fe, Al, Cr, Ga, Co and Mg.

7. The process of claim 6, further comprising separating the condensation products from un-reacted alcohols and gasoline boiling-range hydrocarbons to produce a purified condensation product,
wherein the un-reacted alcohols and gasoline boiling-range hydrocarbons are mixed with gasoline, or optionally, the un-reacted alcohols are recycled to the contacting of step (b).

8. The process of claim 7, further comprising combining the purified condensation product with a diesel or kerosene-type liquid hydrocarbon fuel to produce an improved fuel,
wherein the improved fuel possesses an attribute selected from the group consisting of increased cetane number, decreased emissions of environmental pollutants during combustion and combinations thereof.

9. A process comprising the steps of:
(a) providing a biomass-derived feedstream comprising hydrocarbon mono-functional alcohols that contain five or six carbon atoms;
(b) contacting the feedstream of step (a) with a catalyst in a reactor, wherein the contacting results in an acidic condensation reaction that converts a least a portion of the feedstream to condensation products,
wherein said condensation products comprise at least 10 carbon atoms and at least one ether functional group,
wherein the contacting is conducted at a feedstream flow rate in the range of about 0.1 $h^{-1}$ WHSV to about 20 $h^{-1}$ WHSV;
(c) separating the condensation products from un-reacted alcohols and gasoline boiling-range hydrocarbons to produce a purified condensation product,
wherein the un-reacted alcohols and gasoline boiling-range hydrocarbons are mixed with gasoline or optionally, the un-reacted alcohols are recycled to the contacting of step (b);
(d) combining the purified condensation product with a diesel or kerosene-type liquid hydrocarbon fuel to produce an improved fuel,
wherein the improved fuel possesses an attribute selected from the group consisting of increased cetane number, decreased emissions of environmental pollutants during combustion and combinations thereof
wherein the catalyst comprises a tungstated zirconia with the formula $WO_3/ZrO_2$,
wherein the catalyst is impregnated with one or more promoter metals selected from the group consisting essentially of Ru, Rh, Pa, Au, Ag, Os, Ir, Pt, Fe, Al, Cr, Ga, Co and Mg.

10. The process of claim 9, wherein the catalyst is a microporous molecular sieve selected from the group consisting of crystalline silicoaluminophosphates and aluminosilicates,
wherein the catalyst is impregnated with one or more promoter metals selected from the group consisting essentially of Ru, Rh, Pa, Au, Ag, Os, Ir, Pt, Fe, Al, Cr, Ga, Co and Mg.

11. The process of claim 9, wherein the feedstream of step (a) comprises a member selected from the group consisting of 1-pentanol, 1-hexanol and mixtures thereof.

\* \* \* \* \*